(12) United States Patent
Bisiaux et al.

(10) Patent No.: US 7,429,352 B2
(45) Date of Patent: Sep. 30, 2008

(54) ULTRASOUND SENSOR FOR NON-DESTRUCTIVE CONTROL OF METALLURGICAL PRODUCTS

(75) Inventors: Bernard Bisiaux, Valenciennes (FR); Michel Vahe, Pont-sur-Sambre (FR); Guillaume Cretenot, Saint Romuald (CA)

(73) Assignee: Vallourec & Mannesmann Tubes, Boulogne Billancourt (FR)

( * ) Notice: Subject to any disclaimer, the term of this patent is extended or adjusted under 35 U.S.C. 154(b) by 567 days.

(21) Appl. No.: 10/497,546

(22) PCT Filed: Dec. 11, 2002

(86) PCT No.: PCT/FR02/04296

§ 371 (c)(1),
(2), (4) Date: Mar. 10, 2005

(87) PCT Pub. No.: WO03/050527

PCT Pub. Date: Jun. 19, 2003

(65) Prior Publication Data

US 2005/0156364 A1 Jul. 21, 2005

(30) Foreign Application Priority Data

Dec. 13, 2001 (FR) .................................. 01 16138

(51) Int. Cl.
*C21D 11/00* (2006.01)
*G01N 29/04* (2006.01)

(52) U.S. Cl. .......................................... 266/99; 266/79
(58) Field of Classification Search .................. 266/79, 266/92, 99
See application file for complete search history.

(56) References Cited

U.S. PATENT DOCUMENTS

| 4,404,853 | A | | 9/1983 | Livingston |
| 5,027,659 | A | | 7/1991 | Bele et al. |
| 5,311,127 | A | * | 5/1994 | Bisiaux ....................... 324/232 |
| 5,533,401 | A | | 7/1996 | Gilmore |

FOREIGN PATENT DOCUMENTS

| EP | 0841580 | 5/1998 |
| FR | 2796153 | 1/2001 |
| JP | 59-126952 | 7/1984 |
| JP | 10-332648 | 12/1998 |

* cited by examiner

*Primary Examiner*—Scott Kastler
(74) *Attorney, Agent, or Firm*—Oblon, Spivak, McClelland, Maier & Neustadt, P.C.

(57) ABSTRACT

An installation for non-destructive control for a metal tube in which an ultrasound sensor includes transducer elements that can be excited each at selected times. A downstream circuit for processing the sensed signals analyzes a global response of the tube at ultrasonic excitation. The transducer elements are only excited to produce a single emission and the downstream circuit recovers the samples of the sensed signals each through a transducer element, to associate therewith successive times respectively offset, to calculate plural global responses of the tube at a single emission, by modifying the shifts between the successive times.

25 Claims, 7 Drawing Sheets

ULTRASOUND SENSOR FOR NON-DESTRUCTIVE CONTROL OF METALLURGICAL PRODUCTS

The invention relates to non-destructive control, especially in metallurgy, and more particularly to the non-destructive control of tubes.

The manufacture of tubes is, as far as possible, made completely automatic. When manufacture is complete, the tubes are subjected to a non-destructive control by ultrasound waves, with the aim of selectively detecting one or more defects thereon, using the following tests: surface defects having a substantially longitudinal and/or transverse orientation, on the inside and/or on the outside; defects of thickness and/or in the thickness; the inside and outside diameters are also controlled.

In order to control the entire volume of the tubes, the tubes are subjected to a helical relative movement with respect to the ultrasound sensors and the ultrasound waves are emitted in bursts, at a fast rate, with a firing frequency called a "recurrence" frequency.

The indirect coupling of the sensor to the tube is effected in a liquid, in general water. In practice, in order to detect the various defects mentioned above, sensors having longitudinal ultrasound waves are provided which "sonify" the tube in accordance with various angles of incidence. The angles of incidence are adjusted as a function of numerous parameters, including the dimensions of the tube, its ultrasound transmission properties, the types of defect sought, etc.

The recurrence frequency of the bursts is limited by the outward and return travel time of the ultrasound waves in the coupling liquid and in the metal of the tubes. A long travel time therefore makes it necessary to reduce the recurrence frequency and hence the productivity of the non-destructive control.

According to some known embodiments, the sensors are fixed in position and a helical movement is imparted to the tube.

According to other known embodiments, the ultrasound detectors or sensors are driven in rotation at a rate of a few thousand revolutions per minute about a tube moving at a linear rate which may be as much as approximately one metre per second.

In yet other known embodiments, a sensor is used which is constituted by a multiplicity of ultrasound transducer elements surrounding the tube. The successive excitation of groups of transducer elements makes it possible to proceed with the "formation" of an ultrasound beam with which an angle of incidence on the tube may be associated. The excitation also makes it possible to rotate the beam about the tube by switching the excited groups of elements, and, as a consequence, to replace the above-described mechanical rotation of the sensors by electronic scanning (FR-A-2 796 153).

A particular case of control is that of weldless tubes which are obtained by hot "drilling" bars between cylinders. That manufacturing process leads to defects referred to as "oblique" or defects in the shape of a helix, which exhibit some obliquity relative to the axis of the tube. The obliquity may be positive or negative, depending on the direction of the helix.

The obliquity of the defects depends on the manufacturing range which is used and, in some cases, on the stage of formation of the defect. Thus, the same control installation may therefore have to control defects whose obliquity may vary from −20° to +20°, or more.

The least obliquity brings about major attenuation of the echoes reflected by the defects when the incidence of the beam has been optimised to detect strictly longitudinal defects.

The patent U.S. Pat. No. 3,924,453 describes conventional sensors which cause the ultrasound beam to diverge mechanically in a plane passing through the axis of the tube (so-called "toric divergent" process). The range of obliquity that is detectable is, however, limited.

In addition, the use of multi-element sensors permitting the formation of an ultrasound beam whose deflection is suitable for detecting a given defect obliquity, theoretically enables that problem to be solved. It is therefore expedient to adjust each burst in such a manner that an optimum incidence for a given obliquity corresponds to each burst.

Each burst involves a propagation time in water for outward travel, a propagation time (one outward and return journey, or more) in the tube and, again, a propagation time in the water for return travel. Although it would be possible to multiply the bursts as a function of the number of desired incidences, that technique is in fact hardly applicable industrially, especially owing to the cumulative propagation times which the multiplication of the bursts makes prohibitive. Those cumulative propagation times are physical characteristics which cannot decrease over time.

The invention improves the situation by increasing the productivity of the control installation while at the same time preserving a high level of detectability of defects, in particular defects that are oblique relative to the axis of the tube.

To that end the invention proposes an installation for the non-destructive control of metallurgical products, in particular with indirect coupling, comprising:

an ultrasound sensor device comprising a set of selectively accessible ultrasound transducer elements (Ci), an upstream circuit capable of selectively exciting the transducer elements at selected instants, a downstream circuit capable of collecting the signals sensed on return by the transducer elements, and a processing component (which can be incorporated in the downstream circuit) capable of analysing the signals sensed, as a global response of a metallurgical product to ultrasound excitation.

According to one feature of the installation:

the upstream circuit is arranged to operate by bursts, which are associated with the same temporal law of excitation of the transducer elements, the downstream circuit comprises a memory and is arranged to store samples of the signals sensed (Sij) by each transducer element, in correspondence with each burst, to a selected temporal depth, and the processing component is suitable for co-operating with the memory in order:

for each burst, to read and add up repetitively groups of samples (Sij) corresponding to different transducer elements (Ci), and also to instants (tj) staggered from one element to the other, according to a selected temporal processing law, peculiar to each repetition, which makes it possible to calculate for each burst a plurality of reconstituted responses $(S_T, \alpha_T)$, each of which corresponds to a deflection $\alpha_T$ (multi-processing), and to analyse the global response constituted by those reconstituted responses as a whole.

Thus, a plurality of ultrasound responses each corresponding to a "simulated" incidence, which is selected a posteriori, can be derived from a single burst.

According to one of the advantages afforded by the present invention, the rapidity of the analysis of the metallurgical products is therefore now limited only to the necessary processing times.

In one advantageous embodiment, the downstream circuit comprises a digitalisation unit for the sensed signals, and the memory is arranged to co-operate with the digitalisation unit with a view to storing, as a function of successive instants, on the one hand, and of active transducer elements, on the other hand, the amplitudes of the signals sensed by each transducer element.

In one embodiment, the downstream circuit comprises calculation means capable of defining a distribution of delays to be applied, respectively, to the sensed signals in order to obtain a global response which corresponds to an emission according to a selected beam deflection.

Advantageously, the calculation means are also arranged to take into account the emission characteristics of the transducer elements, such as the convergence of the beams emitted by each element, in the definition of the distribution of the delays to be applied.

The invention is susceptible of different variants, especially the following, which may be combined:

- at each emission burst, the temporal excitation law may not comprise any phase shift between the transducer elements; it may also include such phase shifts; it is also possible to provide for both, that is to say, one burst without a phase shift and one or several bursts with phase shifts, so long as the multi-processing of each burst is preserved.
- the burst(s) with phase shifts may be used to facilitate the definition a posteriori (after multi-processing) of large beam deflections for which the attenuation of the ultrasound waves should be taken into account.
- a helical relative movement is provided for between the tubes and the ultrasound sensor device, by displacing the tube or the sensor or both.
- the sensor may be one-dimensional, that is to say, a linear bar of transducer elements which is arranged substantially parallel with the axis of displacement of the tubes, or a bar which is at least partially arc-shaped (for example in the shape of a truncated cylinder or a truncated sector of a cylinder), and which surrounds the tube.
- the processing component can be arranged to process the return signals by distinct groups of elements of the bar. This constitutes in each case a "virtual sensor", with the aid of a sub-set of the transducer elements of the sensor. Thus, all of the elements of the sensor are fired simultaneously while, at each burst, the signals received by the various virtual sensors are analysed a posteriori, for a (or each) desired phase-shift law.
- the ultrasound sensor device may comprise a two-dimensional network of transducer elements (not necessarily flat). Columns and rows may be distinguished therein. The columns and/or the rows may be used as the above-mentioned one-dimensional sensor. Such a two-dimensional network of sensors is called a "mosaic" network.
- the mosaic sensor can be used to detect oblique defects without a requirement for a physical helical relative displacement because it permits "electronic rotation" of the beam. "Electronic" rotation means a processing of various virtual sensors which is capable of scanning the circumference of the products (at least partially, the complement of rotation being, if necessary, effected by physical displacement). The downstream circuit is therefore arranged to calculate distributions of delays both between the elements of the same row and between the elements of the same column.

Other features and advantages of the invention will emerge on examining the following detailed description and the appended drawings in which.

The following drawings and description basically contain elements of a definitive nature. They can therefore not only be used to make the present invention more understandable but they can also contribute to its definition, where appropriate.

Figure 1:
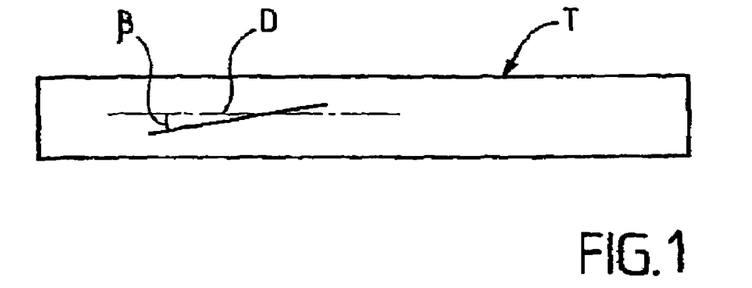
FIG. 1 shows a tube T which has an oblique defect D.

Reference will first of all be made to FIG. 1 in which a tube T leaving a production line has an oblique defect D, of obliquity β relative to the longitudinal axis of the tube. In particular, in a process for manufacturing tubes, without a weld, in which hot-drilling is carried out on metal bars between cylinders, the tubes T occasionally have such defects, in the shape of a helix, with some obliquity β relative to the axis of the tube T.

Figure 2A:
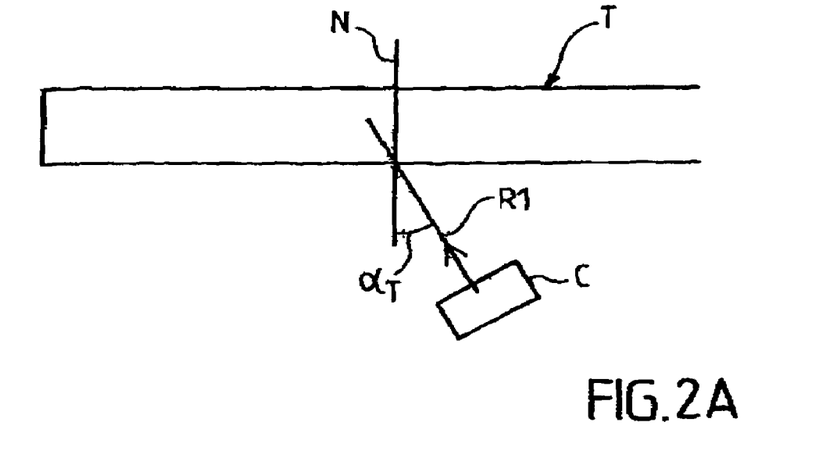
FIG. 2A shows an ultrasound control device with a selected incidence in a longitudinal sectional plane of the tube T, which plane passes through the axis thereof.

Referring to FIG. 2A, a device for the non-destructive control of tubes T comprises a sensor device C which is constituted by one or more ultrasound transducer elements and which "sonifies" the tube T by ultrasound emission at a firing rate, called the recurrence frequency, of, for example, approximately 4 KHz. In principle, the coupling between the ultrasound sensor and the metal tube T is indirect. A column of liquid, in particular water, is generated between the sensor C and the tube, so that the ultrasound waves emitted by the sensor are propagated first of all in the water and then in the tube.

The incidence of the ultrasound beam emitted by the sensors C may be defined, in space, by two angles of incidence. Referring to FIG. 2A, an incident ray R1 forms with a normal N of the tube an angle $\alpha_T$ (axial or longitudinal deflection) in a longitudinal sectional plane of the tube T, which plane comprises the axis of the tube. The second angle enabling a beam incidence to be defined is the angle $\alpha_L$ of FIG. 2B. The ray R1 emitted by the sensor C forms an angle $\alpha_L$ relative to the normal N of the tube T. The angle $\alpha_L$ (transverse deflection) is defined in a transverse sectional plane perpendicular to the axis of the tube T.

Figure 2B:
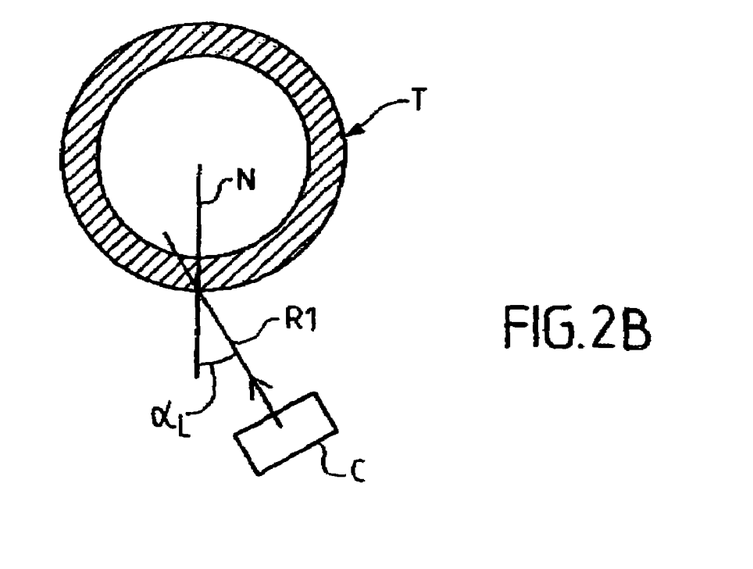
FIG. 2B shows an ultrasound control device with a selected incidence, in a transverse sectional plane of the tube T.

The defect D is in principle located on the outer or inner surface of the tube T or in the vicinity of those surfaces. It comprises a longitudinal component and also a transverse component, the proportion of which is a function of the angle β of the defect. That obliquity β is defined relative to a generatrix of the cylindrical tube T, parallel with the axis of the tube, and may be positive or negative.

The tube itself generally has a relative helical movement with respect to the sensor C in order to control substantially the entire surface of the tube. Along the axis of the tube, the component of the relative helical movement is rectilinear, at a speed which is substantially constant and which may be as much as approximately 1 meter/second. The rotary component of the relative helical movement may be generated by the rotation of the sensor about the axis of the tube or by a rotation of the tube about its axis, the sensor being fixed in position, or else by a combination of those two rotations. In both cases, the sensor is oriented in such a manner that it fires at the tube in accordance with a transverse deflection $\alpha_L$ of approximately 17° in order to detect longitudinal defects or in accordance with an axial deflection $\alpha_T$ of approximately 17° in order to detect transverse defects. Those deflections $\alpha_L$ and $\alpha_T$ have different values for a propagation medium other than water and for tubes made of a material other than steel. The orientation may be fixed (non-adjustable) or may be mechanically adjustable to some extent, but the adjustment is time-consuming and tricky.

In a recent, more developed, technique, a plurality of transducer elements Ci is used (FIG. 3) whose normal is perpendicular to the tube. Respective emission delays τi are applied to the transducer elements in order to create a phase shift between the respective emitted elemental waves Oi, which translates into a difference in travel between the respective emitted waves Ri. The beam that results from all of the waves emitted therefore has a maximum energy in accordance with a deflection α, which is managed electronically by controlling the instant at which the elements Ci emit. It is thus that the totality of the delays τi applied defines a distribution of the delays, called the phase law or temporal law, on the network of sensors Ci and consequently the deflection α of the emission beam resulting from the various waves emitted Ri.

Figures 3, 4, 5:
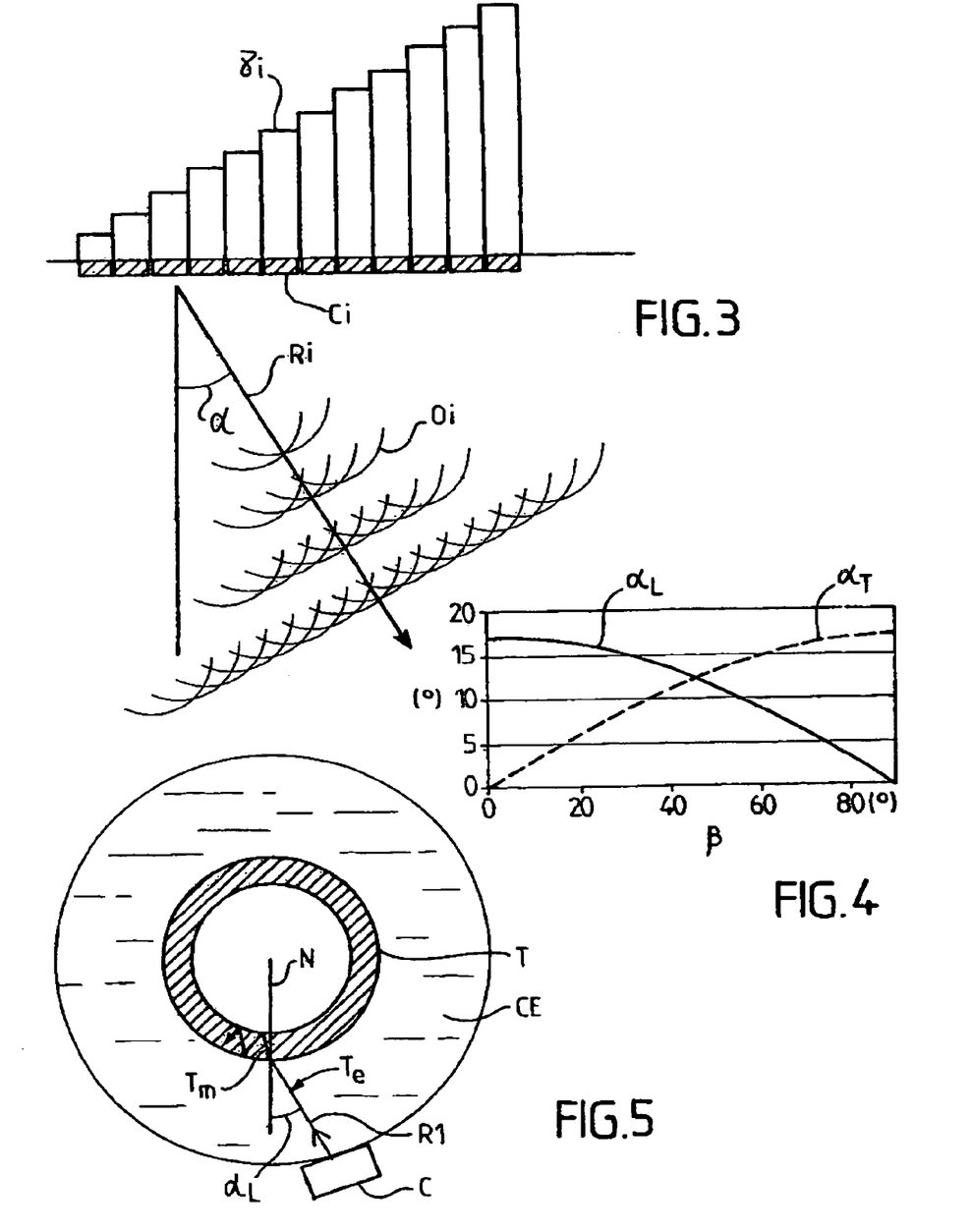
FIG. 3 shows diagrammatically sensors Ci and the delays τi to be applied in order to create a deviation α, a priori, of a ray of ultrasound waves R1.
FIG. 4 represents a graph showing the ultrasound beam incidences to be applied for an obliquity β of a defect present in a tube.
FIG. 5 shows an ultrasound burst, with a column of water CE embodying the interface between the sensor C and the tube T, the ultrasound burst passing first of all through the water and then through the metal of the tube T.

The transducer elements are arranged on a bar. Since the pitch pe between each element Ci is known, it is possible to construct the distribution of the delays to be applied to the emission on the various elements (phase law) to obtain a given deflection α, from the formula (1):

$$\sin \alpha = V.dt/pe$$

in which dt is the delay to be applied between the two consecutive elements and v corresponds to the speed of a longitudinal ultrasound wave in water (V=1490 m·s$^{-1}$). The beam thus formed and deflected by α arrives on the tube in accordance with the incidence α, in other words the angle of incidence on the product is in practice the angle of deflection of the beam.

In order to listen to the signal in an optimum manner, that is to say, in the direction of the incidence of emission, the same phase law is applied to the signals reflected by a defect and received on return by the various elements Ci.

It is also possible to excite successive groups of elements Ci in order to carry out electronic scanning, for example around the tube, if the elements Ci are in the shape of an arc of a circle or the like.

In general, oblique defects are difficult to detect at the same time as longitudinal defects, in particular because an optimised incidence of the beam of ultrasound waves for controlling long defects produces a greatly attenuated response on oblique, and even slightly oblique, defects. For example, the attenuation generally exceeds a factor of 2, for a defect obliquity of 5°. Here an attempt is being made to detect, simultaneously, longitudinal and oblique defects (if possible, with an obliquity of from +35° to −35° at least, without a crippling loss of sensitivity).

The detection of oblique defects therefore requires the adaptation of the angles $\alpha_L$ and $\alpha_T$, which vary with the obliquity of a defect. Referring to FIG. 4, it appears that the optimum for detecting a longitudinal defect (β=0) corresponds to 17° for the angle $\alpha_L$, while the angle $\alpha_T$ is zero. Those values of $\alpha_L$ and $\alpha_T$ are reversed of course for a defect obliquity of 90° (transverse defect). For example, for an obliquity β of 45°, the angles $\alpha_L$ and $\alpha_T$ correspond to deflections of approximately 12°, in a transverse plane and in a longitudinal plane (FIG. 2A and FIG. 2B), respectively.

In fact, for obliquities smaller than 30°, the variations in the angle $\alpha_L$ are relatively small and may be ignored (variation of 3° of angle at most at the beginning of the decrease of $\alpha_L$ as a function of the obliquity β). On the other hand, the introduction of an angle $\alpha_T$ permits the detection of oblique defects, with an obliquity smaller than 30° in absolute value.

Thus, when an attempt is made to detect oblique defects, the value of $\alpha_L$ will be fixed at 17° and $\alpha_T$ will be varied in the longitudinal sectional plane of the tube T, for example within an allowance range of from −10° to +10°, in order to detect the various possible obliquities, including the obliquity zero (longitudinal defects).

In order to detect oblique defects, the patent U.S. Pat. No. 3,924,453 proposes an optical process (called a toric divergent process) which consists in causing the beam to diverge, by means of a lens, in the longitudinal plane of the tube and, on the other hand, in focusing that beam in the perpendicular plane (plane of FIG. 2B). Thus, a relatively limited field of detection is arrived at, of the order of 10° around an obliquity aimed at (−10°<$\alpha_T$<+10°). In addition, that process has the disadvantage of a sensitivity which is variable in accordance with the obliquity. It is thus possible to detect imperfections which would be acceptable and to allow unacceptable defects to pass.

Another process according to the present invention consists in forming a beam deflected by an angle $\alpha_T$ by means of a sensor in the form of a bar which comprises a multiplicity of transducer elements, while the angle $\alpha_L$ is fixed by the configuration of the cell (preferably approximately 17°).

Figure 7:
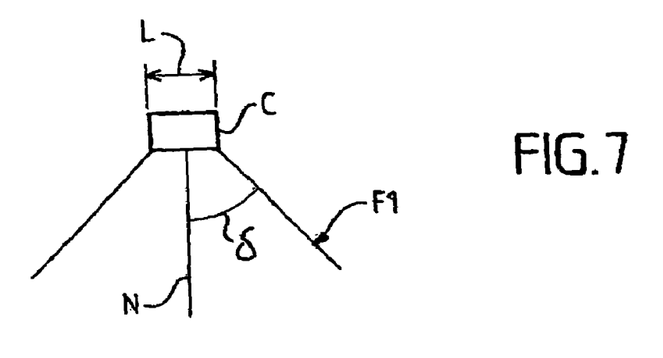
FIG. 7 shows diagrammatically the divergence δ of a beam F1 emitted by an ultrasound sensor C, of a given width L.

Referring to FIG. 7, a sensor C emits a beam F1 of ultrasound waves, the extreme edge of which forms, with the normal to the sensor C, an angle δ, called the angle of divergence (or of opening). The divergence δ is given by the formula (2):

$$\sin \delta = 1.22\, \lambda/L,$$

where λ is the wavelength of the beam in water and L is the width of a transducer element of the sensor (FIG. 7). In any case, the divergence remains greater than the maximum angle $\alpha_T$ (11°) for detecting obliquities of β=30°. That divergence is advantageously used to attain the desired values $\alpha_T$.

For example, for ultrasound waves emitted in water at 5 MHz with elements Ci of width 1.4 mm of a linear bar, δ is approximately 15°.

Using a phase law appropriate to the emission of the elements Ci in accordance with formula (1) and FIG. 3, it is possible to form a beam deflected by an angle $\alpha_T$, so long as the value of $\alpha_T$ is smaller than the divergence δ given by the formula (2). It is then possible to adjust $\alpha_T$ "electronically" by modifying the phase law without it being necessary to orient the sensor in that direction. The same phase law is then applied to the signals received on return and the signals received on return, which have been subjected in that manner to a phase shift, are added up to obtain a maximised global response.

That process, envisaged by the Applicant, makes it possible to aim at a given obliquity, with a correct and known sensitivity, and to have a homogeneous response for the various possible obliquities of the tube defects. The table in annex A1 contains the results of preliminary tests in respect of the deflection $\alpha_T$ of the beam with a view to detecting oblique defects (multi-burst method).

More precisely, the results relate to the amplitude of the echoes obtained on return for various obliquities of defect and various values of deflection $\alpha_T$ of the beam and to the amplification gain values of the signals. The values indicated in bold correspond to the deflection values to be used to detect a given obliquity. It will be appreciated that the results obtained for the amplification gains are satisfactory (23.5 dB for the notch at 25°).

It is also possible to compensate for the variation in detection sensitivity as a function of the deflection used and therefore to provide a uniform sensitivity for detecting defects irrespective of their obliquity.

On the other hand, for each obliquity aimed at, it is necessary to carry out a grouped firing of the transducer elements of the sensor. Thus, if several defect obliquities are sought, the same number of ultrasound bursts has to be provided since a delay law specific to emission and reception has to be provided for each obliquity aimed at.

Referring to FIG. 5, an ultrasound burst R1 is composed of travel through water $T_e$ followed by travel through the tube $T_m$ (useful travel), those travels having durations proportional to the thickness of the materials passed through. For acoustic reasons, the column of water CE which covers the interface between the sensor C and the tube T is such that the travel time in the water is greater than the travel time in the metal of the tube.

In particular, the total time of an ultrasound burst $T_t$ is $$T_t = T_e + T_m, \text{ with } T_e > T_m.$$

Applied to the multi-burst detection of oblique defects, if n is the total number of obliquities aimed at, the total time $T_t$ becomes:

$$T_t = n \cdot (T_e + T_m)$$

For conventional industrial firing rates (close to 4 KHz in order to carry out a simple control of longitudinal defects), it is possible to detect only approximately one or two obliquities, in addition to the longitudinal defects by the multiple burst technique in the case of relatively thick tubes (approximately 36 mm thick), taking into account the propagation times of the ultrasound beams.

The detection of oblique defects in accordance with the present invention is based on yet another principle.

According to the invention, the transducer elements Ci of a linear bar arranged parallel with the axis of the tube are controlled in such a manner that, on emission, all of the elements are activated at the same time (substantially without a phase shift). In other words, the "physical deflection on emission" is zero. On the other hand, a "virtual" deflection of the beam is constructed on the return signals by staggering the instants at which the received signals are added up, for each element Ci.

Figure 6:
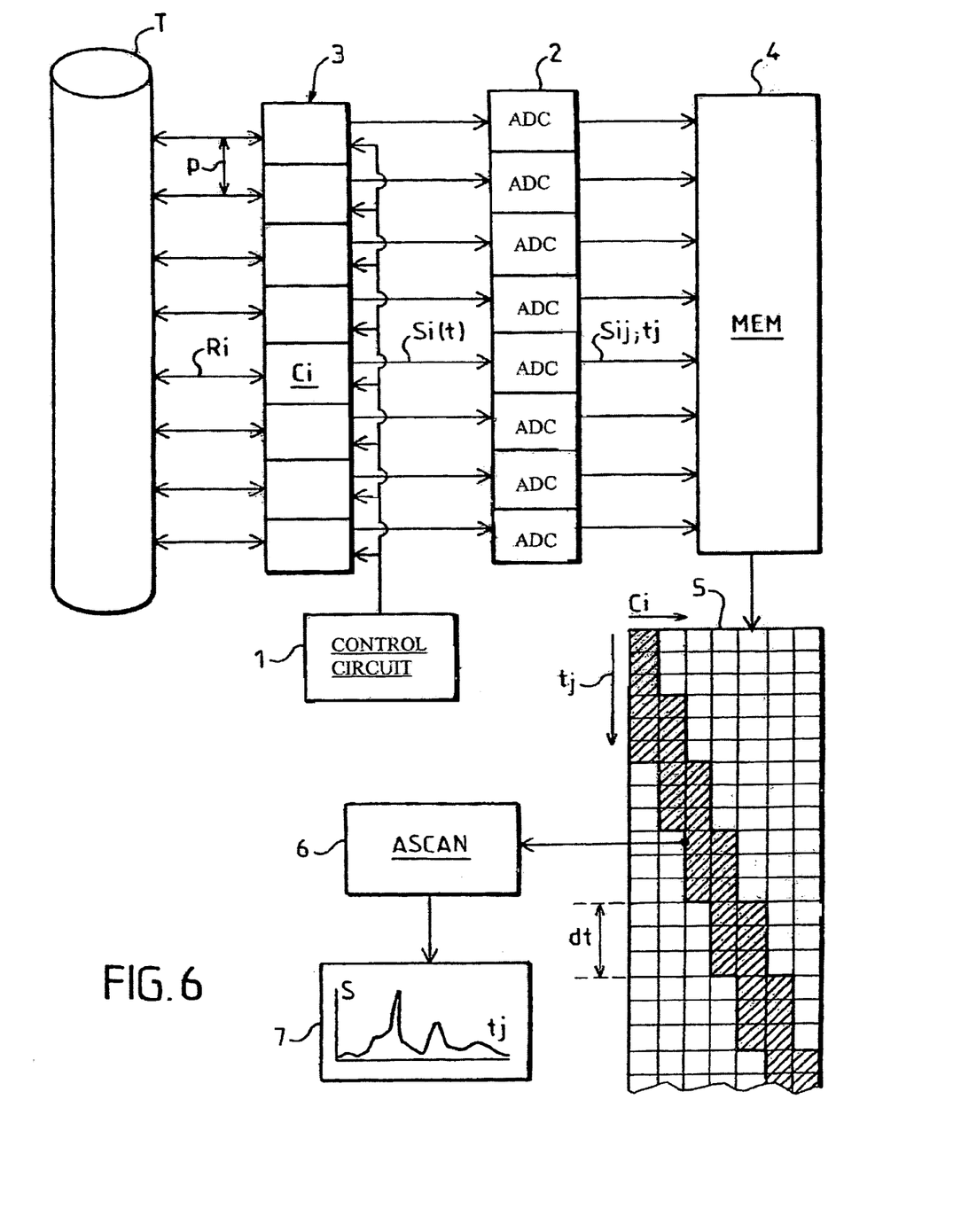
FIG. 6 shows diagrammatically an installation for detecting defects, in accordance with the present invention.

Referring to FIG. 6, the transducer elements Ci of the sensor are arranged, in the example described, along a bar 3. The bar is fixed in position in the control installation and its general direction is parallel with the axis of the tube T to be controlled. The bar is inclined by an angle $\alpha_L$ of approximately 17° relative to the normal to the tube in a transverse sectional plane of the tube T (plane of FIG. 2B) and a helical movement is imparted to the tube T along its axis. The angle $\alpha_L$ of 17° corresponds to the optimum angle $\alpha_L$ for detecting defects having a small obliquity (β less than approximately 30°).

The elements Ci are excited by a control circuit 1 each to emit an ultrasound pulse wave Ri having an ultrasound frequency of the order of 5 MHz. Preferably, the elements Ci are controlled in such a manner that they emit at the same time, that is to say, substantially without a phase shift. The ultrasound waves reflected by a defect and sensed on return by each element Ci are converted into electrical signals Si(t). Those analog signals Si(t) are converted, respectively, by analog-to-digital converters 2, operating, for example, at 10 times the ultrasound frequency, that is to say, 50 MHz.

The analog-to-digital converters 2 are connected to a memory 4 for storing, to a temporal depth of several tens of microseconds, digital data which constitute signal samples Sij (for example in respect of amplitude) and which are associated, respectively, with instants tj. In the notation Sij, the index i corresponds to an identifier of element Ci in the bar 3, while the index j corresponds to an identifier of instant tj.

A calculation module in the installation selects from the memory 4 a plurality of signal samples Sij which are staggered, on the one hand, as a function of the index i of the elements Ci and, on the other hand, as a function of the successive instants tj and adds up the staggered signal samples. The addition may be effected, for example, in instantaneous amplitude or in any other appropriate manner.

The frame carrying the reference 5 in FIG. 6 illustrates, by way of example, the manner in which the calculations are carried out and also illustrates the structure of the memory 4.

The member 5 may be regarded as a processing circuit or component (or as a processing module, without the word module implying any individualisation).

The memory 4 is preferably arranged in addresses associated with a column index i (corresponding to the elements Ci) and with a line index j (corresponding to the successive instants tj).

The processing module 5 calculates the delays dt to be applied between successive columns i, according to formula (1), by the deflection $\alpha_T$:

$$dt = pe \cdot \sin \alpha_T / V$$

The delay values dt are of the order of several tens of nanoseconds.

The processing module then selects, with a precision of the order of a nanosecond, values of Sij, from a set of columns of elements Ci, which are staggered temporally. It then adds up those samples at each instant tj in order to define a reconstituted response signal for the deflection $\alpha_T$:

$$S_{ij}(\alpha_T) = S_{1,j} + S_{2,j+2dt} + S_{3,j+4dt} + \ldots + S_{n,j+2(n-1)dt}$$

Such an addition makes it possible to bring back into phase, at the transducer elements, signals that were emitted at the same moment and that have undergone travels with travel times which differ in respect of dt in the outward journey and in respect of dt on the return journey between two elements.

After calculating the value of dt according to formula (1), the addition carried out above is used to maximise the energy of the beam in the direction of the deflection $\alpha_T$.

The table in annex A2 contains the results of tests of deflection $\alpha_T$ of the beam for detecting oblique defects, by the method according to the present invention. It enables the double deflection values ($2\alpha_T$) corresponding to phase shifts of (2dt) on the outward journey and on the return journey to be determined. For different obliquities, the value ($2\alpha_T$) to be used corresponds to the amplitude values indicated in bold in the table. The table also provides the gain values for the various values of $\alpha_T$. Those values are acceptable even for large values of $\alpha_T$.

Figure 8:
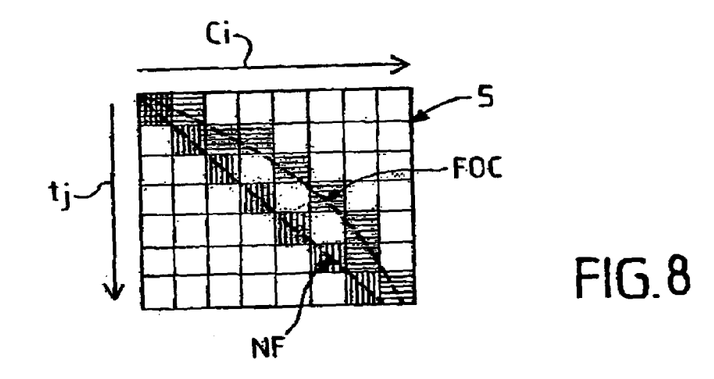
FIG. 8 shows diagrammatically the selected intensities in the signals received, without taking into account focusing applied to the ultrasound beam (vertical hatching) and taking into account that focusing (horizontal hatching)

In the above, consideration has been given to a constant temporal difference dt between the successive instants tj, which corresponds to a linear delay law NF (FIG. 8) with dt constant. However, that law does not take into account a focusing which may be applied to the beam of ultrasound waves on the tube. In order to take that focusing into account in the delay law, the phase shift dt decreases to a minimum and then increases to the initial value. Referring to FIG. 8, the selected intensities Sij form, for a time tj, in the matrix 5 of columns Ci and rows tj, a curved line FOC.

The processing means enable a reconstituted response for various deflection angles $\alpha_T$ to be calculated.

The module 6 of the installation recovers the signals of reconstituted responses St($\alpha_T$) in order to shape a signal which can be used directly by a display device 7 (display screen or the like). The device 7 then represents a signal called "A-SCAN" comprising pulses of ultrasound echoes, which pulses are reconstituted as a function of time and for one or more selected deflections $\alpha_T$.

According to one of the advantages afforded by the present invention, the total time $T_t$ taken to aim at n obliquities, with the notations used above, is then given by:

$$T_t = T_e + T_m + n \cdot T_{calc},$$

$T_{calc}$ being the calculation time which may be expressed as a function of $T_m$, and hence $$T_t = T_e + n \cdot G \cdot T_m,$$

where G is a coefficient representing the processing rate of the chain comprising the analog-to-digital converters, the memory 4, the selection of intensities from the set of stored intensities etc. Thus, the lower G is, the higher is the processing rate.

According to one of the advantages afforded by the present invention, the travel time in water for (n-1) obliquities is thus suppressed.

With current electronic and computer means, G is always less than 1 and may be less than 0.5 with ultra-rapid electronic systems. Thus, the limitations are no longer acoustic but electronic because the limiting factor becomes, in the present invention, the calculation time necessitated by the above processing operations. The limitations are therefore no longer physical but evolutive with the advances in the rapidity of electronic circuits.

Figure 9:
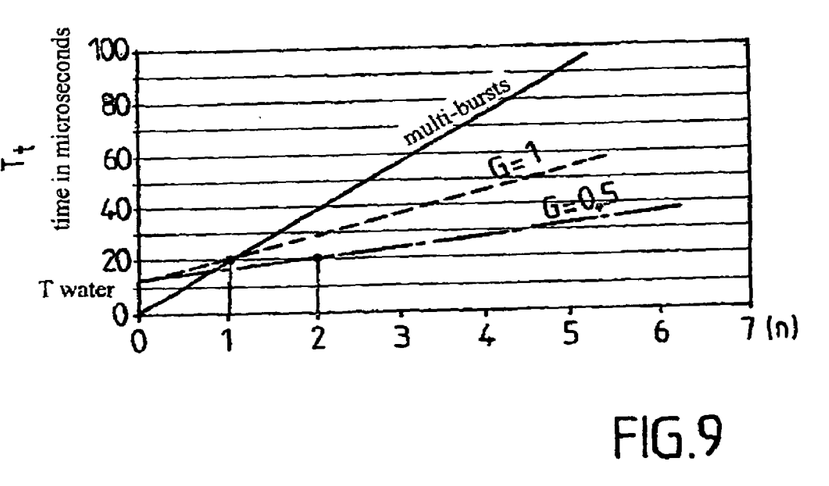
FIG. 9 is a graph of the global propagation times of the ultrasound waves and the calculation times (ordinate in microseconds) as a function of the number of defect obliquities that can be detected (on the abscissa), in accordance with the technique of the prior art (short and long broken lines) and according to the invention (continuous line) and by an optimised process, in accordance with the present invention (broken lines)

FIG. 9 represents, for a given tube thickness, the total times Tt for detecting oblique defects, as a function of the number of obliquities controlled n. The graph is prepared using the technique of the prior art with demultiplication of the bursts (phase shift between the elements Ci, as of emission, for each deflection $\alpha_T$, which corresponds to the curve with long and short broken lines). The technique according to the invention is also used with a factor G of 1 (solid-line curve) relative to a standard electronic system and with a factor G of 0.5 (dotted-line curve) relative to an ultra-rapid electronic system.

It will thus be appreciated that the smaller factor G is, the shorter is the time necessary to aim at several obliquities, which enables the tube control rate to be increased, in particular in a chain for controlling tubes after they have been machined.

The sensor device has a length adapted to the control pitch of the installation, that is to say, a length of the order of 100 mm in the example. The defects to be detected have a length which may be distinctly smaller, for example 20 mm. A defect of length 100 mm, that is to say, of a length equivalent to the bar (3), creates a signal on each of the elements of the bar and therefore an intense reconstituted signal, by addition. On the other hand, a defect of 20 mm creates a signal on 20% of the elements of the bar and therefore a reconstituted signal which is 5 times less intense than that for a defect of 100 mm.

A not incompatible imperfection 100 mm long may therefore be detected and a defect of 20 mm may be detected slightly or not at all.

In order to compensate for that disadvantage, a solution is used which consists in carrying out the processing on only a few elements of the bar, for the same firing of all the elements of the bar. For example, the processing may be carried out on an arrangement of 8 elements of a bar of 64 elements, and the processing can be started again on other arrangements of 8 elements of the bar. The group of 8 elements is called a "virtual sensor".

Each arrangement gives correctly, after adding up the signals Sij on the 8 elements, a signal of the elemental reconstituted response for the deflection $\alpha_T$. It is possible to retain as the global reconstituted response, the elemental reconstituted signal among the reconstituted signals of the various arrangements that has a maximum peak amplitude. Each arrangement of "virtual sensor" elements is derived from the previous arrangement by translation by a pitch pi, called the imbrication pitch.

Let $N_T$ be the total number of elements in the bar and let $N_v$ be the number of transducer elements in the virtual sensor. When the imbrication pitch is from 1 to $N_v$, while remaining strictly less than $N_v$, there is an overlapping or imbrication of the arrangements of the virtual sensor. When the imbrication pitch pi is equal to $N_v$, the arrangements of the sensor are disposed side by side. When the imbrication pitch is greater than $N_v$ and less than $N_T$, the various arrangements do not totally cover the elements of the sensor.

The processing of the signals on the $N_v$ elements of the virtual sensor is carried out a maximum number of times. The number of possible arrangements is given by the formula (3):

$$N = \text{truncation } \{(N_T - N_v)/pi\} + 1$$

For example,
 if $N_T = 64$, $N_v = 8$ and $pi = 1$, then $N = 57$. In that case, two successive arrangements have 7 elements in common.
 if $N_T = 64$, $N_v = 8$ and $pi = 8$, then $N = 57$. In that case, two successive arrangements have no common element.
 if $N_T = 64$, $N_v = 8$ and $pi = 4$, then $N = 57$. In that case, two successive arrangements have 4 elements in common, which corresponds to 50% coverage of the successive arrangements.

After retaining as the global reconstituted response of the N arrangements, the one that has a maximum peak amplitude for the deflection $\alpha_T$ sought, it is in the same way possible to carry out the calculations for other values of the deflection $\alpha_T$.

By way of variation, it is possible first of all to determine the various signals of the elemental reconstituted response for various angles $\alpha_T$ and a virtual sensor arrangement and then to carry out the same calculations for the other arrangements.

In any case, the global reconstituted response for a given deflection is determined, retaining the elemental response that provides a maximum peak amplitude for that deflection.

When the arrangements of virtual sensors that are located at the ends of the bar are processed, the response signal is disturbed by the absence of elements on each side of the virtual sensor. That is why it is preferable to eliminate $(N_v/2)$ elements at each end of the bar, from the various virtual sensor arrangements.

The maximum number of arrangements is therefore reduced to $$N' = \text{truncation } \{(N_T - 2N_v)/pi\} + 1$$

As shown by the table of annex A2, the global reconstituted signal is amplified in a different manner for each value of $\alpha_T$ so that the rigour of the control operation is the same for the various values of $\alpha_T$.

By way of variation, the amplification gain may be uniform, while the triggering threshold of the defect is adapted to each value $\alpha_T$.

The Applicant has carried out "static" tests for controlling oblique defects, on a steel tube 96 mm in diameter and 12 mm thick. Notches of approximately 5% of the thickness of the tube were formed in order to simulate oblique defects. The obliquity of the notches is from 0° to 25° and their length in the longitudinal direction is approximately 12 mm.

The sensors used are marketed by the company Imasonic under the name Imasonic (registered trademark). The pitch pe between the elements is 1.5 mm (with 1.4 mm of width L for one element). The device comprises a total of 32 elements, with a mechanical focusing of 50 mm in water. In an example of a cell used, the deflection $\alpha_L$ may be fixed mechanically at 17°. The electronic system used is an electronic system of RDTech make of the type Focus 32/128 which is capable of managing 32 elements in parallel.

Bearing in mind the geometry of the transducer elements, their divergence $\delta$ is of the order of 15° and is entirely suitable for the deflection values to be used in order to detect oblique defects for an obliquity of from −25° to +25°.

The static tests were carried out using a virtual sensor of 8 elements for analysing the return signal. The defect is disposed at right-angles to the virtual sensor. Such a virtual sensor has a listening length of approximately 9 mm, which is very suitable for the length of the defect being studied (12 mm).

Figure 10:
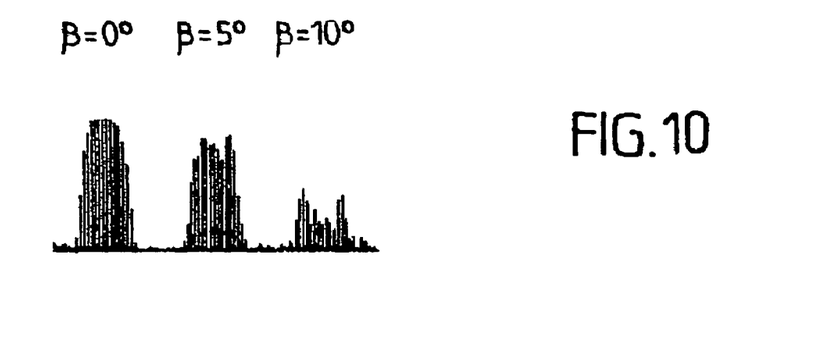
FIG. 10 shows the amplitude of a signal received (from a non-deviated initial beam) for several obliquities β of a defect detected with a sensor according to FIG. 6 and a standard sensor used in a conventional technique (curves with dotted line)

Referring to FIG. 10, the attenuation of the response of a notch as a function of its obliquity (0°, 5° or 10°) is smaller than that obtained with conventional sensors having a single element approximately 10 mm wide. Typically, for a conventional sensor, the attenuation is at least 5 dB for a notch of 5°, while the sensors used here undergo an attenuation of less than 1 dB for the same notch obliquity.

Figure 11:
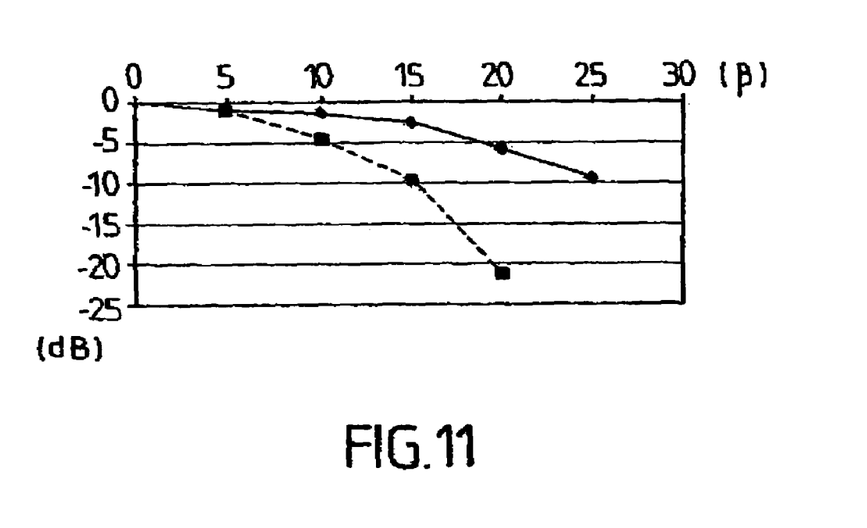
FIG. 11 shows the loss of sensitivity (by acoustic attenuation) for large obliquities aimed at, with the technique of demultiplied bursts (curve with solid line) and the single-burst technique according to the invention (curve with dotted line)

However, for obliquities $\beta$ greater than +20° or less than −20° (FIG. 11), the Applicant noticed a slightly lesser sensitivity in the signals of the reconstituted response (installation according to the invention) compared with the case where a multi-burst installation would be used, with the same type of bar and with in each case a burst according to the preferred obliquity sought, which gives an "adapted emission-reception travel".

In fact, in the installation according to the invention, there is no delivery onto the defect of a beam deflected a priori (on emission) by the preferred angle $\alpha$, as may be effected in a multi-burst installation; the invention proceeds merely by phase restoration of the signals received, when they arrive on the transducer elements. Those received signals include the component reflected (strictly, "back-scattered") by the defect; and it is the phase restoration which enables the elemental response, and then the global response, to be reconstituted for a given deflection $\alpha_T$.

However, that phase restoration on reception relates to signals that have not been correspondingly brought into phase on emission. It follows that it relates to received signals which have not been subjected exactly to the "adapted emission-reception travel". As a general rule, the tests carried out by the Applicant have shown that, under normal operating conditions, the relative attenuation (from one sensor element to the other) which results from that difference in travel was sufficiently small to remain negligible, at the very least in a specific range of obliquities.

The gain to be used in the installation according to the invention is not, however, incompatible and, in addition, the gain in control productivity for several obliquities largely counterbalances the disadvantage on the lesser sensitivity.

Figure 10A:
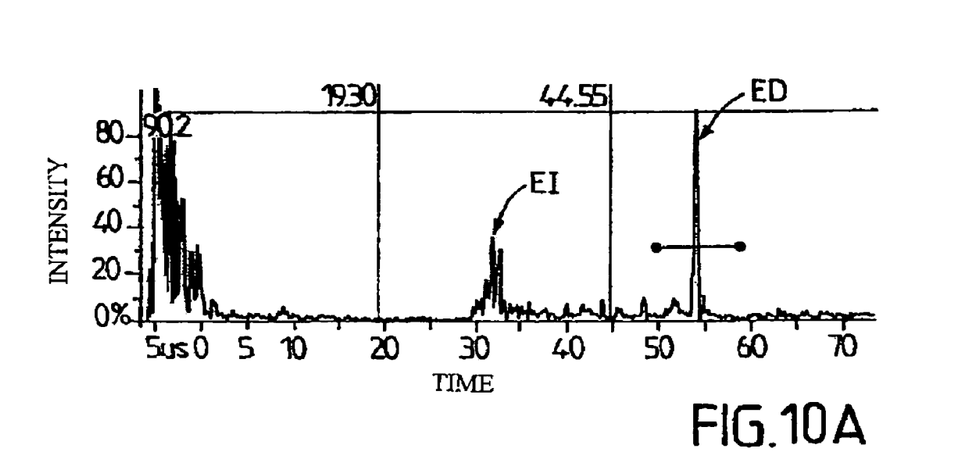
FIGS. 10B and 10A are A-SCAN signal curves obtained on oblique defects by a technique according to the invention and by a technique of de-multiplied bursts of the prior art, respectively.
Figure 10B:
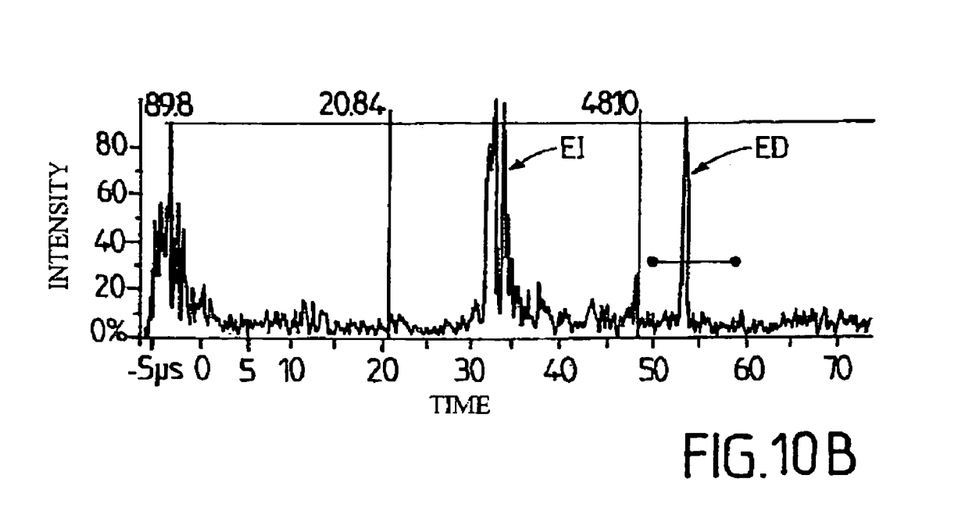

FIGS. 10A and 10B show an A-SCAN recording of the same defect having an obliquity of 20°, on a multi-burst installation and on a so-called "post-acquisition" processing installation according to the invention, respectively. FIGS. 10A and 10B show that the two types of installation enable the 20° oblique defect to be detected in a similar manner; in those Figures, the signal EI denotes the water-steel interface echo and the signal ED denotes the defect echo. The straight-line segment having an amplitude of 30% corresponds to the defect criterion (temporal gate and intensity).

The Applicant has also carried out dynamic tests in order to determine, in particular, the useful detection regions of the virtual sensors. The dynamic tests were carried out on the same tubes as above but with a notch 20 mm long having an obliquity $\beta = 0°$ in order to determine the detection holes. Thus, the obliquity of the defect has no influence on the measurement. The tests were carried out using the same equipment as for the static tests and a mechanical installation cell of the type with adjustment of the angle $\alpha_L$. The angle $\alpha_L$ has been optimised on the signal stemming from an external longitudinal defect ($\beta = 0°$). The Applicant also used a Sofranel 5052GPD gate with a frequency band of 4-12 MHz.

Figure 14:
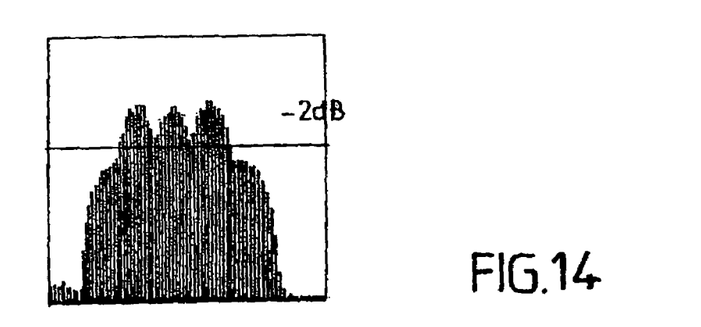
FIG. 14 shows the response of a notch as a function of the relative positions of the notch and the bar, for virtual sensors that are juxtaposed and composed of 8 elements.
Figure 15:
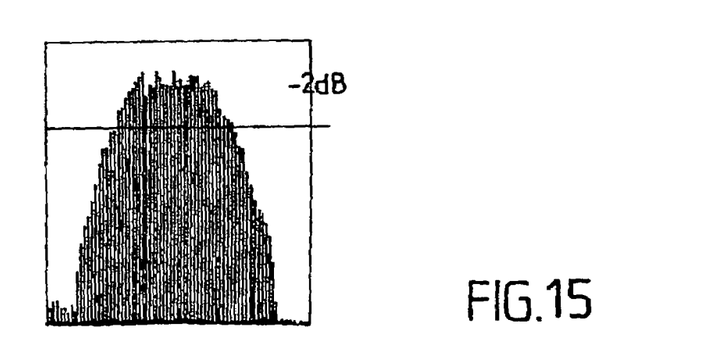
FIG. 15 shows the response of a notch as a function of the relative positions of the notch and the bar, for 50%-imbricated virtual sensors composed of 8 elements.

FIGS. 14 and 15 show the response of the 20-mm notch as a function of the relative positions of the notch and of the bar of 32 elements having a total length of 48 mm, for two series of arrangements of virtual sensor composed of 8 elements.

For an imbrication pitch pi=8 elements, the immediate successive arrangements do not cover one another and do not overlap one another, as in the conventional configuration with detectors having a diameter of 15 mm.

FIG. 14 shows a useful sensor region at −2 dB of 31 mm, that is to say, 65% of the bar; the detection holes are lower than 1.5 dB and have a length sufficiently small not to impair the detection of notches 25 mm long.

For an imbrication pitch pi=4 elements, the immediate successive arrangements cover one another or overlap one another to the extent of 50%. No more detection holes are found but the number of arrangements and the calculation times are also doubled.

The static and dynamic tests carried out show that the installation with post-acquisition processing according to the invention enables obliquity defects of from −20° to 20° to be detected.

In order to achieve obliquity values higher than 20°, it is possible to use the installation and the methodology with post-acquisition processing by carrying out a phase shift on the single firing of all of the elements of the sensor device in order to form a beam having a non-zero "physical deflection on emission", for example of 5°.

The processing of the signals sensed on return is similar to the processing described above, which comprises storage of the Sij samples, a selection of the Sij values staggered in accordance with a delay law and an addition of those staggered values for each calculation of a reconstituted response under a deflection $\alpha_T$. The signal returned by the defect is then less attenuated for the large deflections $\alpha_T$ and it is possible to exploit the capacities of divergence δ of the elements Ci of the bar in the best manner.

However, that method has some disadvantages because the optimisation of the deflection $\alpha_L$ is no longer effected on a straight defect (β=0°) but on a defect having an obliquity of 20°. In addition, the method does not enable the major positive and negative obliquities to be detected, and the displacement of the virtual sensor arrangements may be rendered more complex by the use of bursts with a phase shift on emission.

Figure 12:
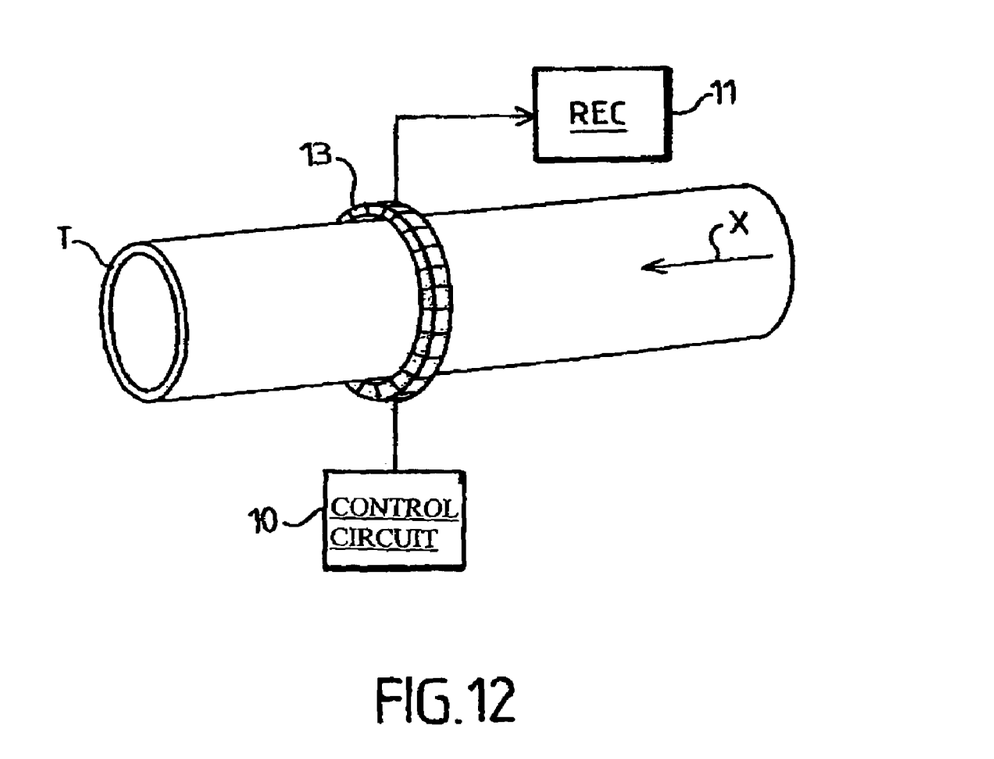
FIG. 12 shows an ultrasound control device in an embodiment using an arc-shaped sensor.

FIG. 12 represents another embodiment of an installation according to the invention which is intended to control longitudinal defects on tubes. According to that Figure, the sensor device is constituted by a linear bar 13 in the shape of an arc of a circle and the various elements of the sensor are arranged along the arc. The tubes T to be controlled are moved along their axis and the plane of the bar is perpendicular to the axis of the tubes. Firing is carried out on all of the $N_T$ elements of the sensor, with or without a phase shift between elements. The same post-acquisition processing as that described above is carried out in order to determine a reconstituted response for a given deflection $\alpha_L$, and for various virtual sensors in the bar, in order to effect, for example, an electronic rotation of the beam about the tube, as indicated above.

Figure 13:
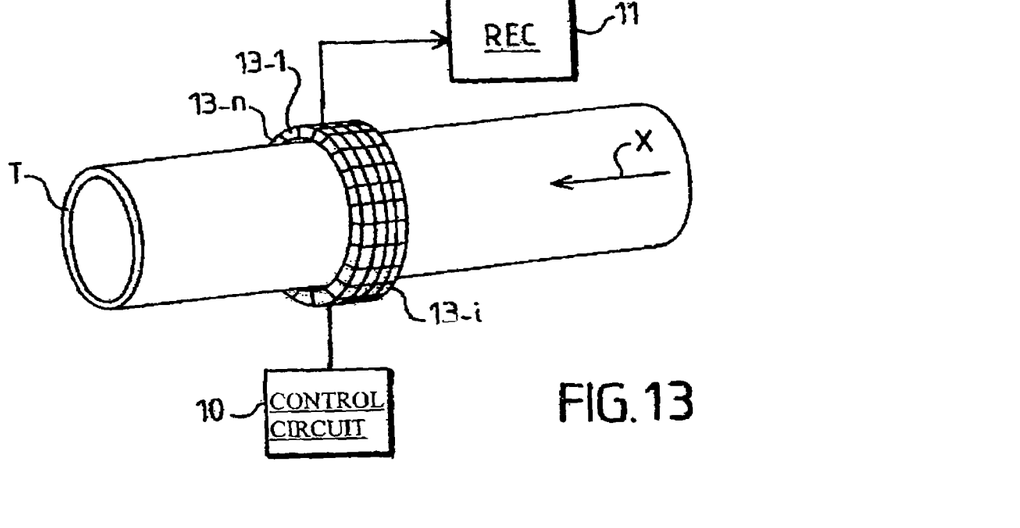
FIG. 13 shows an ultrasound control device in an embodiment using a "mosaic" sensor.

FIG. 13 represents yet another embodiment according to the invention. In that Figure, the sensor device is arranged on a cylindrical surface and is constituted by a mosaic or by a network of elements arranged in rows which are parallel with one another, for example 13-1, ... 13-i, ... 13-n, as illustrated. In the example, each row is a generatrix of the cylindrical surface of the sensor. The tubes to be controlled are displaced along their axis coaxially with the cylindrical surface of the sensor.

In FIGS. 12 and 13, the control circuit (or upstream circuit, for emission) is marked 10, and the reception assembly (or downstream circuit) is marked 13.

The upstream circuit 10 is arranged to produce the same firing of all of the transducer elements, with or without a phase shift between adjacent elements. In the case of FIG. 13, for example, it is possible to carry out a phase shift between successive rows in order to form a beam inclined in an optimum manner in the cross-sectional plane of the tubes (deflection $\alpha_L$ of approximately 17°), but without a phase shift between elements of the same row, and to effect an electronic rotation of the beam about the tube using different virtual sensors.

Post-acquisition processing is carried out on the return signals which have been stored, according to the invention, in order to reconstitute a response signal for optimised angles $\alpha_L$ (approximately 17°) and angles $\alpha_T$ of from −5° to +5°. Such an installation having a mosaic sensor enables several defect obliquities to be controlled at a fast rate (from −20° to 20°) with a rectilinear advance of the tubes in the installation, unlike the previously described installations which use a helical advance to detect oblique defects.

It is also possible to select in that installation, laws for deflecting, in a variable but selected manner, the return beam in accordance with a cross-section of the tubes or in accordance with a longitudinal plane of the tubes in order to optimise the angles $\alpha_T$ and $\alpha_L$ (for example $\alpha_T$=17° with $\alpha_T$=0°, $\alpha_T$=13° with $\alpha_T$=11°).

It is possible to use two-dimensional virtual sensors in that installation. In that case, the sensors are displaced by an imbrication pitch pi having an axial component and a circumferential component.

The installations described have in common their capacity to increase the control rate by effecting a single post-acquisition processing of the return signals. It is possible to simplify the examples described and likewise the combinations of the features of the examples described, especially as a function of the types of control which it is desired to carry out, together or separately.

| | | A1 | | | | | | |
|---|---|---|---|---|---|---|---|---|
| Deflection | Gain | Amplitude of the echo on the notch according to obliquity (%) | | | | | | |
| $\alpha_1$ (°) | (dB) | 0 | 5 | 10 | 15 | 20 | 25 | 45 |
| 0 | 14.4 | 90 | 50 | 10 | | | | |
| 1 | 15.4 | 70 | 90 | 40 | 15 | | | |
| 3 | 15.8 | 10 | 55 | 90 | 55 | 20 | | |
| 4 | 16.8 | | 20 | 75 | 90 | 30 | 10 | |
| 5 | 20 | | | 55 | >100 | 90 | 30 | |
| 7 | 23.5 | | | 10 | 40 | 83 | 90 | |

| | | A2 | | | | | | |
|---|---|---|---|---|---|---|---|---|
| Double Deflection | Gain | Amplitude of the echo on the notch according to obliquity (%) | | | | | | |
| 2 $\alpha_T$(°) | (dB) | 0 | 5 | 10 | 15 | 20 | 25 | 45 |
| 0 | 11 | 90 | 53 | 10 | | | | |
| 3 | 12 | 20 | 90 | 20 | | | | |
| 6 | 15.5 | | 20 | 90 | 10 | | | |
| 8 | 20.5 | 25 | 20 | 35 | 90 | 10 | | |
| 11 | 32.2 | 80 | 50 | 35 | 50 | 90 | | |

-continued

| | | A2 | | | | | | |
|---|---|---|---|---|---|---|---|---|
| Double Deflection | Gain | Amplitude of the echo on the notch according to obliquity (%) | | | | | | |
| $2\alpha_T(°)$ | (dB) | 0 | 5 | 10 | 15 | 20 | 25 | 45 |
| 16 | 40 | >100 | >100 | 90 | 65 | 65 | 70 | |

The invention claimed is:

1. An installation for non-destructive control of metallurgical products, comprising:
  an ultrasound sensor device comprising a set of selectively accessible ultrasound transducer elements;
  an upstream circuit configured to selectively excite the transducer elements at selected instants;
  a downstream circuit configured to collect signals sensed on return by the transducer elements; and
  a processing component configured to analyze the signals sensed, as a global response of a metallurgical product to ultrasound excitation;
  wherein the upstream circuit is configured to operate by bursts, which are associated with a same temporal law of excitation of the transducer elements,
  wherein the downstream circuit comprises a memory and is configured to store samples of the signals sensed by each transducer element, in correspondence with each burst, to a selected temporal depth,
  wherein the processing component is configured to cooperate with the memory and is further configured, for each burst, to read and add up repetitively groups of samples corresponding to different transducer elements, and also to instants staggered from one element to another, according to a selected temporal processing law, peculiar to each repetition, wherein said processing component is further configured to calculate for each burst a plurality of reconstituted responses, each of which corresponds to a deflection on emission, and wherein said processing component is further configured to analyze the global response constituted by the reconstituted responses as a whole.

2. An installation according to claim 1, wherein the ultrasound transducer elements have a divergence at least equal to a maximum angle of deflection, for the reconstituted responses.

3. An installation according to claim 2, wherein the downstream circuit comprises a digitalization unit for the signals sensed by each of the transducer elements of the sensor device.

4. An installation according to claim 3, wherein the memory is arranged to cooperate with the digitalization unit for storing, as a function of successive instants, and active transducer elements, the samples of the signals sensed by each transducer element.

5. An installation according to claim 4, wherein the processing component comprises means for defining distributions of delays applied, respectively, to the sensed signals, and for obtaining, for each distribution, a reconstituted response that correspond to a burst according to a selected beam deflection.

6. An installation according to claim 4, wherein the processing component comprises means for gaining access to the memory as a function of times associated with the samples, for each transducer element.

7. An installation according to claim 1, wherein the upstream circuit is further configured to excite the transducer elements, substantially without a phase shift between them, in accordance with a temporal excitation law.

8. An installation according to claim 1, wherein the upstream circuit is further configured to excite the transducer elements in accordance with a temporal excitation law such that said transducer elements have, between them, phase shifts defining a beam deflected on emission, and wherein, based on the temporal excitation law, the processing component is further configured to define distributions of delays to be applied to the sensed signals, taking into account the phase shifts between transducer elements on excitation, so that the reconstituted responses each correspond to a deflection centered around an angle of physical deflection of the beam on emission.

9. An installation according to claim 1, wherein said processing component is further configured to consider each group of samples added up as corresponding to a selected sub-set of transducer elements, as a virtual sensor.

10. An installation according to claim 9, wherein the processing component is further configured to calculate plural elemental reconstituted responses of a product to a same burst under a same deflection, for different sub-sets of the virtual sensor.

11. An installation according to claim 10, wherein the processing component is further configured to calculate the reconstituted response in a form of a function of the elemental reconstituted responses for the same deflection and for different sub-sets of the virtual sensor.

12. An installation according to claim 11, wherein the reconstituted response of the product to the burst under a deflection is the elemental response that has a maximum peak amplitude.

13. An installation according to claim 9, wherein the processing component is configured to calculate reconstituted responses for different deflections, with different sub-sets of the sensor device.

14. An installation according to claim 9, wherein the sub-sets of the sensor device, for calculating a reconstituted response of the product to the burst under a deflection, comprise substantially a same number ($N_v$) of transducer elements.

15. An installation according to claim 14, wherein the sub-sets of the sensor device are selected from the sensor device while excluding at each end a guard band, of which a number of transducer elements is approximately half a number of transducer elements of a sub-set.

16. An installation according to claim 14, wherein two consecutive sub-sets are derived from one another by a translation by an imbrication pitch.

17. An installation according to claim 16, wherein two consecutive sub-sets comprise common elements.

18. An installation according to claim 16, wherein said processing component is further configured to consider the selected number of sub-sets of the sensor device for calculating a reconstituted response under a deflection as corresponding to substantially to a maximum number of possible sub-sets for the selected imbrication pitch and for a number $N_v$ of elements selected from ($N_T$-$N_v$) elements.

19. An installation according to claim 1, for control of metallurgical products of steel tube type, further comprising:
  means for actuating the steel tubes in accordance with a helical movement about an axis of the steel tubes, wherein the ultrasound sensor device is constructed in a form of a linear bar of transducer elements disposed substantially parallel with the axis of the steel tubes and arranged such that the ultrasound beam on emission has a selected deflection in a cross-sectional plane of the steel tubes.

20. An installation according to claim 1, for control of metallurgical products of steel tube type, further comprising:
means for actuating the steel tubes in accordance with a rectilinear movement along their axis, wherein the ultrasound sensor device is constructed in a form of a linear bar of transducer elements disposed substantially parallel with the axis of the steel tubes and arranged such that the ultrasound beam on emission has a selected deflection in a cross-sectional plane of the steel tubes, the bar being set in rotation about the steel tubes.

21. An installation according to claim 1, for control of metallurgical products of steel tube type, further comprising:
means for actuating the steel tubes in accordance with a rectilinear movement along their axis, and wherein the ultrasound sensor device is constructed in a form of a bar of transducer elements, substantially in a shape of an arc of a circle, arranged around the steel tubes.

22. An installation according to claim 1, further comprising:
means for actuating tubes in accordance with a rectilinear movement along their axis,
wherein the ultrasound sensor device comprises a network of transducer elements arranged substantially in accordance with a cylindrical surface coaxial with the tubes, in plural rows of elements, which rows are parallel with one another and with the axis of the tubes, and
wherein the downstream circuit and the processing component are configured to determine distributions of delays on the signals sensed on return by the transducer elements of a sub-set or of the whole of the network.

23. An installation according to claim 1, wherein the processing component is incorporated in the downstream circuit.

24. An installation for non-destructive control of metallurgical products, comprising:
an ultrasound sensor device comprising a set of selectively accessible ultrasound transducer elements;
an upstream circuit that selectively excites the transducer elements at selected instants;
a downstream circuit that collects signals sensed on return by the transducer elements; and
a processing component that analyzes the signals sensed, as a global response of a metallurgical product to ultrasound excitation;
wherein the upstream circuit operates by bursts, which are associated with a same temporal law of excitation of the transducer elements,
wherein the downstream circuit comprises a memory that stores samples of the signals sensed by each transducer element, in correspondence with each burst, to a selected temporal depth,
wherein the processing component cooperates with the memory, for each burst, reads and adds up repetitively groups of samples corresponding to different transducer elements, and also to instants staggered from one element to another, according to a selected temporal processing law, peculiar to each repetition, wherein said processing component further calculates for each burst a plurality of reconstituted responses, each of which corresponds to a deflection on emission, and wherein said processing component further analyzes the global response constituted by the reconstituted responses as a whole.

25. An installation for non-destructive control of metallurgical products, comprising:
an ultrasound sensor device comprising a set of selectively accessible ultrasound transducer elements;
an upstream means for selectively exciting the transducer elements at selected instants;
a downstream means for collecting signals sensed on return by the transducer elements; and
a processing means for analyzing the signals sensed, as a global response of a metallurgical product to ultrasound excitation;
wherein the upstream means comprises means for operating by bursts, which are associated with a same temporal law of excitation of the transducer elements,
wherein the downstream means comprises a memory for storing samples of the signals sensed by each transducer element, in correspondence with each burst, to a selected temporal depth,
wherein the processing means comprises means for cooperating with the memory, and for each burst, means for reading and adding up repetitively groups of samples corresponding to different transducer elements, and also to instants staggered from one element to another, according to a selected temporal processing law, peculiar to each repetition, wherein said processing means further comprises means for calculating for each burst a plurality of reconstituted responses, each of which corresponds to a deflection on emission, and wherein said processing means further comprises means for analyzing the global response constituted by the reconstituted responses as a whole.

* * * * *